US011992316B2

(12) United States Patent
Gavas et al.

(10) Patent No.: US 11,992,316 B2
(45) Date of Patent: May 28, 2024

(54) SYSTEM AND METHOD FOR EYE-BLINK BASED ASSESSMENT OF SUSTAINED VISUAL ATTENTION OF A TARGET

(71) Applicant: Tata Consultancy Services Limited, Mumbai (IN)

(72) Inventors: Rahul Dasharath Gavas, Bangalore (IN); Mithun Basaralu Sheshachala, Bangalore (IN); Debatri Chatterjee, Kolkata (IN); Ramesh Kumar Ramakrishnan, Bangalore (IN); Venkata Subramanian Viraraghavan, Bangalore (IN); Achanna Anil Kumar, Bangalore (IN); Girish Mariswamy Chandra, Bangalore (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 601 days.

(21) Appl. No.: 17/213,371

(22) Filed: Mar. 26, 2021

(65) Prior Publication Data

US 2022/0061723 A1   Mar. 3, 2022

(30) Foreign Application Priority Data

Sep. 3, 2020   (IN) .............................. 202021038081

(51) Int. Cl.
*A61B 5/16* (2006.01)
*A61B 5/00* (2006.01)
(52) U.S. Cl.
CPC ............ *A61B 5/163* (2017.08); *A61B 5/0075* (2013.01); *A61B 5/0077* (2013.01)

(58) Field of Classification Search
CPC ..... A61B 5/163; A61B 5/0075; A61B 5/0077; A61B 5/113; A61B 5/378
(Continued)

(56) References Cited

U.S. PATENT DOCUMENTS 9,510,752 B2 * 12/2016 Klin .................. A61B 5/165
10,209,773 B2 * 2/2019 Khaderi ................ A61B 5/369
(Continued)

OTHER PUBLICATIONS

Lenskiy et al., "Blink Rate Variability during resting and reading sessions," Neurons and Cognition (2016).
(Continued)

*Primary Examiner* — Mohammed A Hasan
(74) *Attorney, Agent, or Firm* — FINNEGAN, HENDERSON, FARABOW, GARRETT & DUNNER LLP (57) ABSTRACT

This disclosure relates generally to a method and system for assessment of sustained visual attention of a target. The conventional methods utilize various markers for assessment of attention, however, blink rate variability (BRV) series signal is not explored yet. In an embodiment, the disclosed method utilizes BRV series signal for assessing sustained visual attention of a target. A gaze data of the target is recorded using an eye tracker and a set of uniformly sampled BRV series signal is reconstructed from each of the BRV series. One or more frequency domain features, including pareto frequency, are extracted from the set of uniformly sampled BRV series signal. The values of frequency domain features extracted from the set of BRV series signals are compared with corresponding threshold values to determine visual sustained attention of the target.

17 Claims, 5 Drawing Sheets

(58) Field of Classification Search
USPC .......................................................... 351/209
See application file for complete search history.

(56) References Cited

U.S. PATENT DOCUMENTS 10,602,972 B2    3/2020  Super
2022/0071535 A1* 3/2022  Jernigan ............ A61B 5/02405

OTHER PUBLICATIONS

Ren et al., "Comparison of the Use of Blink Rate and Blink Rate Variability for Mental State Recognition," IEEE Transactions on Neural Systems and Rehabilitation Engineering, 27(5):867-875 (2019).

* cited by examiner

SYSTEM AND METHOD FOR EYE-BLINK BASED ASSESSMENT OF SUSTAINED VISUAL ATTENTION OF A TARGET

PRIORITY CLAIM

This U.S. patent application claims priority under 35 U.S.C. § 119 to: India Application No. 202021038081, filed on Sep. 3, 2020. The entire contents of the aforementioned application are incorporated herein by reference.

TECHNICAL FIELD

The disclosure herein generally relates to assessment of visual sustained attention of a target, and, more particularly, to system and method for assessment of visual sustained attention of a target using blink rate variability (BRV) series associated with gaze data of the target.

BACKGROUND

Attention is an important visual function by which important information can be selected and irrelevant information can be filtered out. Multiple brain centers of a user act in conjunction for selecting the most relevant information. Mainly there are two types of attention—(i) passive attention and (ii) active attention. Passive attention is an involuntary process triggered by external stimuli like bright flash, strong odor which are sensed by the primary sense organs. Active attention is a voluntary process guided by alertness, effort and concentration. Active attention is a multidimensional cognitive process involving ability to maintain the focus on the important information.

Active attention can again be classified into four categories—i) sustained attention ii) selective attention iii) divided attention and iv) alternating attention. Both sustained and selective attention are needed when we focus on a particular thing. Inability to maintain the focused attention is an indicator of cognitive dysfunction and hence, is treated as an early indicator of cognitive decline. Therefore, assessment of visual attention is important.

Visual attention can be measured using various modalities like questionnaire, psychological tests and physiological sensing. Physiological parameters like heart rate, skin conductance level, respiration rate, brain signals etc. are used as a bio-marker of attention. Recently, eye blinks have been reported to be a potential marker of attention. Features like blink rate, magnitude of blinks are closely related to attentional control. Eye blinks can be detected from an assortment of physiological sensing, viz. electroencephalogram (EEG), nearable eye trackers based on infrared, wearable eye trackers, electro-occulogram (EOG), electro-myograph (EMG) and video cameras. Detection of blinks using video camera or nearable eye trackers makes it possible to deploy such systems in real time scenarios as they are cheap and unobtrusive in nature.

SUMMARY

Embodiments of the present disclosure present technological improvements as solutions to one or more of the above-mentioned technical problems recognized by the inventors in conventional systems. For example, in one embodiment, a method for eye-blink based assessment of sustained visual attention of a target is provided. The method includes recording gaze data of the target using an eye tracker, via one or more hardware processors, the gaze data comprising data associated with eye-blink response of the target during a systematic execution of a set of visual tasks. Further, the method includes reconstructing from the gaze data, a set of uniformly sampled blink rate variability (BRV) series signal via the one or more hardware processors, each of the BRV series signal comprises a time series constructed from intervals between consecutive eye-blinks obtained during the systematic execution of a set of visual tasks. Furthermore, the method includes extracting, via the one or more hardware processors, one or more time and frequency domain features from the set of uniformly sampled BRV series signal, wherein the one or more frequency domain features comprises at least a pareto frequency feature. Also, the method includes comparing values of extracted one or more features of the set of BRV signals with a threshold values of the one or more features that are indicative of visual attention via the one or more hardware processors. Moreover, the method includes determining, via the one or more hardware processors, sustained visual attention of the target based on the comparison.

In another aspect, a system for eye-blink based assessment of sustained visual attention of a target is provided. The system includes a memory storing instructions, one or more communication interfaces; and one or more hardware processors coupled to the memory via the one or more communication interfaces, wherein the one or more hardware processors are configured by the instructions to record gaze data of the target using an eye tracker, the gaze data comprising data associated with eye-blink response of the target during a systematic execution of a set of visual tasks. The one or more hardware processors are further configured by the instructions to reconstruct from the gaze data, a set of uniformly sampled blink rate variability (BRV) series signal, each of the BRV series signal comprises a time series constructed from intervals between consecutive eye-blinks obtained during the systematic execution of a set of visual tasks. Further, the one or more hardware processors are configured by the instructions to extract one or more time and frequency domain features from the set of uniformly sampled BRV series signals, wherein the one or more frequency domain features comprises at least a pareto frequency feature. Also, the one or more hardware processors are configured by the instructions to compare values of extracted one or more features of the set of BRV signals with a threshold values of the one or more features that are indicative of visual attention. Moreover, the one or more hardware processors are further configured by the instructions to determine visual sustained attention of the target based on the comparison.

In yet another aspect, a non-transitory computer readable medium for eye-blink based assessment of visual sustained attention of a target is provided. The method includes recording gaze data of the target using an eye tracker, via one or more hardware processors, the gaze data comprising data associated with eye-blink response of the target during a systematic execution of a set of visual tasks. Further, the method includes reconstructing from the gaze data, a set of uniformly sampled blink rate variability (BRV) series signal via the one or more hardware processors, each of the BRV series signal comprises a time series constructed from intervals between consecutive eye-blinks obtained during the systematic execution of a set of visual tasks. Furthermore, the method includes extracting, via the one or more hardware processors, one or more time and frequency domain features from the set of uniformly sampled BRV series signals, wherein the one or more frequency domain features comprises at least a pareto frequency feature. Also, the method includes comparing values of extracted one or more features of the set of BRV signals with a threshold values of the one or more features that are indicative of visual attention via the one or more hardware processors. Moreover, the method includes determining, via the one or more hardware processors, visual sustained attention of the target based on the comparison.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Visual attention is linked with cognitive functions involving learning and memory. Impaired visual attention is an early indicator of cognitive dysfunction and memory loss. It plays a crucial role for development of executive functions and emotions. For measuring sustained attention, neuropsychologists use scientifically validated tests like digit span-forward task, trail making task, tests of variables of attention. These tests require expert intervention for scoring and interpretation. For quantitative assessment of attention, studies have been conducted using brain signals. Other physiological parameters like heart rate, respiration etc., have also been used for the assessment of attention. Electro-oculogram signals are most widely used approach for measurement of attention.

Various features like blink rate, blink amplitude, blink frequency are closely associated with attention level. A known study utilized the concept of extracting blink rate variability (BRV) signals for reading tasks. The study was further extended in for resting and reading tasks. They reported that the average inter-blink duration is higher for reading tasks and is associated with mental workload. Another known study analyzed the inter-relationships between episodic memory and the inter-eye blink intervals (IEBI) while watching a movie. The memory performance correlated positively with IEBI and thus the authors state that IEBI is a reliable marker of concentration. However, the study does not state the nature of variability in the IEBI. In a known method, the blink rate variability was analyzed for reading and memory tasks, of which, the number of blinks were less for the reading task and a high standard deviation was noticed in the BRV associated with the memory task. It was also reported that the BRV decreases for tasks demanding more attention or mental activity. Another known technique showed that BRV at rest correlated well with a subject's performance in an IQ test. Still another conventional method showed the usability of time and frequency domain features of BRV in distinguishing low and high cognitive load levels. Frequency sub-bands were extracted using discreet wavelet transform, however, no proper information of these band ranges was found. However, the aforementioned techniques are limited in determining appropriate frequency regions of BRV series signals that can be indicative of visual attention.

Various embodiments disclose method and system for assessment of visual sustained attention of a target using BRV series signal. In an embodiment, the disclosed method and system are capable of determining appropriate frequency regions of BRV signals that can be indicative of visual attention. The blink rate variability (BRV) which is defined as variability of the inter-blink durations, is used for analyzing sustained attention for visual tasks. In an embodiment, uniformly sampled BRV series is reconstructed from the gaze data recorded using an eye tracker. A number of features are extracted from this series.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Referring now to the drawings, and more particularly to FIG. 1 through 7B, where similar reference characters denote corresponding features consistently throughout the figures, there are shown preferred embodiments and these embodiments are described in the context of the following exemplary system and/or method.

Figure 1:
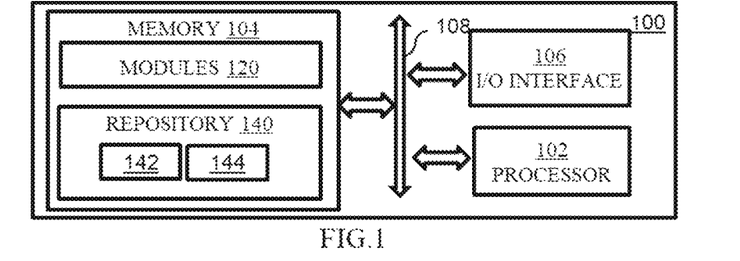
FIG. 1 illustrates a block diagram of a system for eye-blink based assessment of visual sustained attention of a target, according to some embodiments of the present disclosure.

FIG. 1 illustrates a block diagram of a system 100 for eye-blink based assessment of sustained visual attention of a target, according to some embodiments of the present disclosure. The system is capable of reconstructing a uniformly sampled BRV series signal from the gaze data recorded using an eye tracker. Based on the gazed data, variability of the inter-blink durations, termed as blink rate variability (BRV) series signal is determined. A number of features, and more particularly, a pareto frequency feature is extracted from the BRV series signal, for analyzing sustained attention for visual tasks.

The system 100 includes or is otherwise in communication with one or more hardware processors such as a processor 102, at least one memory such as a memory 104, and an I/O interface 106. The processor 102, memory 104, and the I/O interface 106 may be coupled by a system bus such as a system bus 108 or a similar mechanism. The I/O interface 106 may include a variety of software and hardware interfaces, for example, a web interface, a graphical user interface, and the like The interfaces 106 may include a variety of software and hardware interfaces, for example, interfaces for peripheral device(s), such as a keyboard, a mouse, an external memory, a camera device, and a printer. Further, the interfaces 106 may enable the system 200 to communicate with other devices, such as web servers and external databases. The interfaces 106 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 106 may include one or more ports for connecting a number of computing systems with one another or to another server computer. The I/O interface 106 may include one or more ports for connecting a number of devices to one another or to another server.

The hardware processor 102 may be implemented as one or more microprocessors, microcomputers, microcontrollers, digital signal processors, central processing units, state machines, logic circuitries, and/or any devices that manipulate signals based on operational instructions. Among other capabilities, the hardware processor 102 is configured to fetch and execute computer-readable instructions stored in the memory 104.

The memory 104 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 104 includes a plurality of modules 120 and a repository 140 for storing data processed, received, and generated by one or more of the modules 120. The modules 120 may include routines, programs, objects, components, data structures, and so on, which perform particular tasks or implement particular abstract data types.

The repository 140, amongst other things, includes a system database 142 and other data 144. The other data 144 may include data generated as a result of the execution of one or more modules in the other modules 130. In an embodiment, the repository 140 may include a privacy policy repository and a video repository. The PP repository may include a plurality of privacy policy segments obtained from a plurality of PPs. The plurality of PPs may be obtained from existing organizations and/or online services. The video repository may include a plurality of video templates or video snippets in various formats. The plurality of PP segments and the plurality of video templates shall further be explained in the description below.

Figure 2:
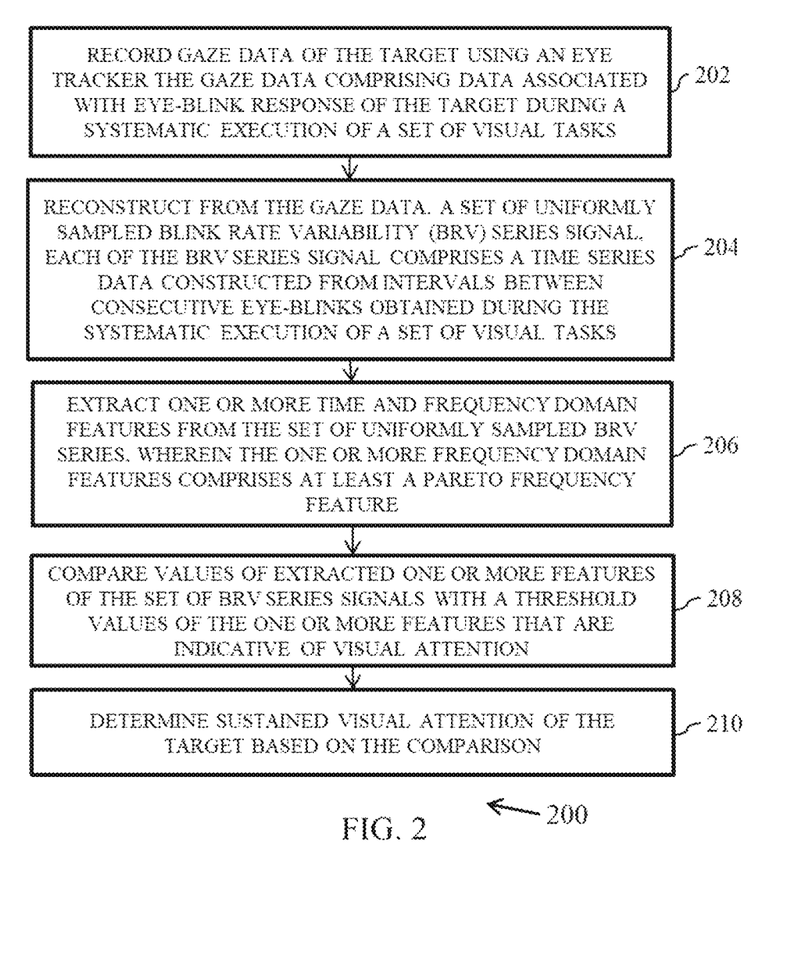
FIG. 2 is a flow diagram of a method for eye-blink based assessment of visual sustained attention of a target in accordance with an example embodiment of the present disclosure.

Referring to FIG. 2, a flow diagram of a method 200 for eye-blink based assessment of visual sustained attention of a target is described in accordance with an example embodiment. The method 200 depicted in the flow chart may be executed by a system, for example, the system, 100 of FIG. 1. In an example embodiment, the system 100 may be embodied in a computing device.

Operations of the flowchart, and combinations of operation in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 200 are described with help of system 100. However, the operations of the method 200 can be described and/or practiced by using any other system.

At 202 of the method 200, the disclosed system 100 records gaze data of the target using an eye tracker, via one or more hardware processors. In an embodiment, the gaze data may be recorded using one of an Infrared based eye tracker and a camera-based eye tracker. In an embodiment, the gaze data includes data associated with eye-blink response of the target during a systematic execution of a set of visual tasks. An example of systematic execution of a set of visual tasks is described further with reference to FIGS. 3A-3B in the description below.

At 204, the method 200 includes reconstructing from the gaze data, a set of uniformly sampled blink rate variability (BRV) series signal via the one or more hardware processors. Each of the BRV series signal includes a time series constructed from intervals between consecutive eye-blinks obtained during the systematic execution of the set of visual tasks. In an embodiment, reconstructing the uniformly sampled BRV series signal is performed by oversampling and interpolation on the gaze data. Herein, it is assumed that the blinks occur at samples kn, where $n \in \{0, 1, \ldots, N-1\}$ indexes the blinks.

The sequence is defined as: $y[ln]=(k_{n+1}-k_n)$,
where $ln=M(k_{n+1}+k_n)/2$ and M=10 is the oversampling factor.

The oversampling is required because the sequence does not have a uniform sampling interval. This sequence, $\{y[ln]\}$ is interpolated using a cubic model to obtain the BRV signal sampled at 300 Hz, $y[l]$, $l \in \{0, 1, \ldots, L-1\}$, where $L \approx Mk_{N-1}$. An example of the oversampling and the interpolated curve is illustrated and described further with reference to FIGS. 4A-4B.

At 206, the method 200 includes extracting, via the one or more hardware processors, one or more frequency domain features from the set of uniformly sampled BRV series signals. Herein, the one or more frequency domain features includes at least a pareto frequency feature. Additionally or alternatively, the one or more frequency domain features may include frequency, power at mean frequency, dominant frequency, power at dominant frequency and total power. The pareto frequency feature includes a frequency range within which 80% of cumulative power of a frequency spectrum of the BRV series signal resides. In an embodiment, the system 100 computes a cumulative sum of powers up to 80% of the total power, and this value is thus taken as the pareto frequency.

At 208, the method 200 includes comparing values of extracted one or more features of the set of BRV signals with a threshold values of the one or more features that are indicative of visual attention via the one or more hardware processors. In an embodiment, the threshold value of the pareto frequency feature indicative of the visual attention is less than or equal to 0.1 Hz.

At 210, the method 200 includes determining, via the one or more hardware processors, visual sustained attention of the target based on the comparison. For example, for a target if the value of the pareto frequency is determined to be less than 0.1, then the target may be considered to have a sustained attention.

Figure 3A:
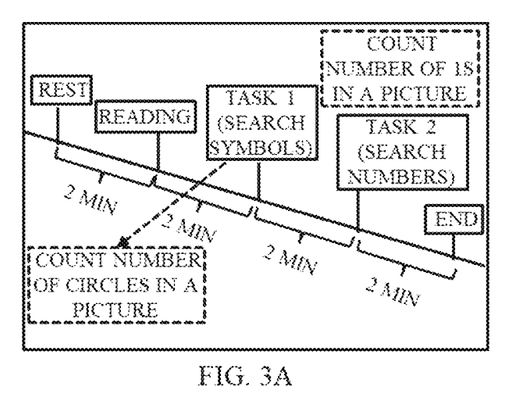
FIGS. 3A-3B illustrates an example scenario of presenting stimulus to targets for assessing eye-blink based of visual sustained attention of a target in accordance with some embodiments of the present disclosure.
Figure 3B:
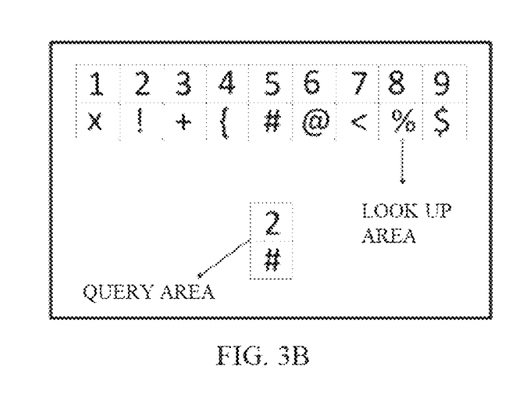

An example of determination of the visual sustained attention of the target is described further with reference to FIGS. 3A-3B Example Scenario In an example scenario for visual sustained attention of a target using eye blink data of targets. For the aforementioned purpose, two sets of stimulus were maintained for visual attention. The first stimulus (Stimulus 1) included Reading and Visual Search Task. Herein, a combination of reading and visual search task was to be performed in the sequence as shown in FIG. 3A. An initial 2 minutes rest period is provided wherein the participant is asked to freely gaze on the screen in a relaxed manner. They were instructed not to close their eyes as it would prevent us from collecting the blink data. Next, a reading task was introduced, wherein the detail experimental procedure and steps to be performed were presented on the screen word by word. This lasted for 2 minutes. Next, two types of visual search tasks were used. In task 1, the participants are instructed to search and count a given symbol among randomly scattered symbols. In task 2, participants were to count the number of occurrences of a target number. Sample snapshots of task 1 and 2 are shown in FIG. 3A. Each of these tasks lasted for a duration of two minutes. The objective of giving the tasks systematically was to isolate attention from mental workload and hence identified tasks that were very simple to execute and yet required attention.

The second stimulus (Stimulus 2) included a Digitized Digit Symbol Substitution Test. The Digit Symbol Substitution Test (DSST) is a psychological test for working memory, visual attention, processing speed. It is particularly used to track above mentioned abilities for traumatic brain injury patients and geriatric population. When administered on healthy individuals, only visual attention varies whereas other cognitive abilities remain more or less constant. The present experiment used a computerized version of the test. FIG. 3B shows the screen layout for the same. The look up table (LUA) was presented at the top of the screen contains target digit-symbol pair. The query digit symbol pair appeared at the query area (QA). The participants had to match the entries of QA with that of LUA. When the QA pair matches with the LUA pair, then the participants responded with a keypress. Each query pair was shown for a duration of 3 seconds. There were three variants of the test: (i) Version 1—where the entries of LUA are fixed and only the QA entries changes with each trial. This version is analogous to the pen-paper DSST test. (ii) Version 2—where the entries of both LUA and QA changes and (iii) Version 3—where the entries in LUA is fixed, QA entries and the QA locations change with trials.

For the purpose of said experiment, twelve participants volunteered for the study involving Stimulus 1 (mean age: 29.25±6 years, 4 Females). A separate set of twenty-two participants volunteered for Stimulus 2 (mean age: 39±13.55 years, 7 Females). All the participants belong to different projects of our research lab and are devoid of any cognitive impairments. They all had normal or corrected to normal vision with glasses. The experiments are conducted in a closed room under constant and stable lighting condition. The stimuli are shown on a computer screen placed at a distance of 60 cm from the participant. EyeTribe™ eye tracker was used for collecting eye gaze data. A chin rest was used to minimize the head movements during data collection. The gaze data was collected at a sampling rate of 30 Hz with the eye tracker placed below the computer screen.

Eye tracker data collected during execution of tasks was processed to construct the BRV signal. EyeTribe™ dumps the events in time as zeros when the pupil could not be detected.

Apart from blinking, there might be a number of reasons like glitches in the device hardware, lighting effects, head movements, and so on, wherein the pupil could not be detected. These instances where zeros are dumped were extracted. Typical average blink duration for human eye is 200 ms to 450 ms which includes both full blink and half blinks. In the present case, it was assumed that the blink duration should be at least 100 ms. As the sampling frequency of the device is 30 Hz, this assumption mandates that if there are at least 3 consecutive zeros in the raw event data, then that can be treated as eye blinks.

Figure 4A:
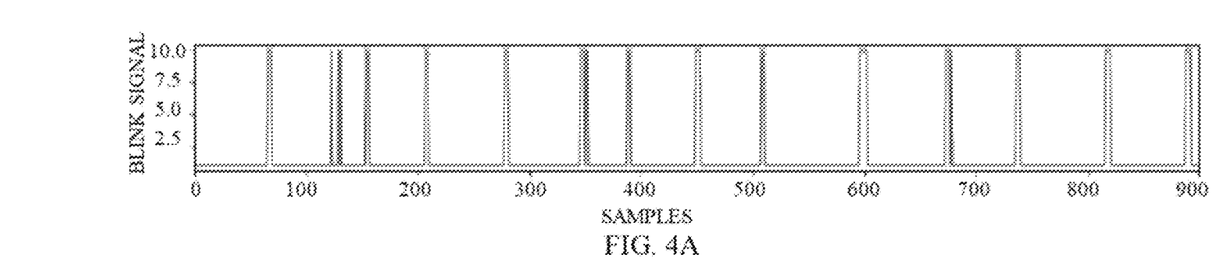
FIGS. 4A-4C illustrates BRV series signal construction from the blink signal involving peaks for the detected blinks in time, interpolated BRV signal and spectrum of the signal (in FIG. 4B), respectively in accordance with some embodiments of the present disclosure.
Figure 4B:
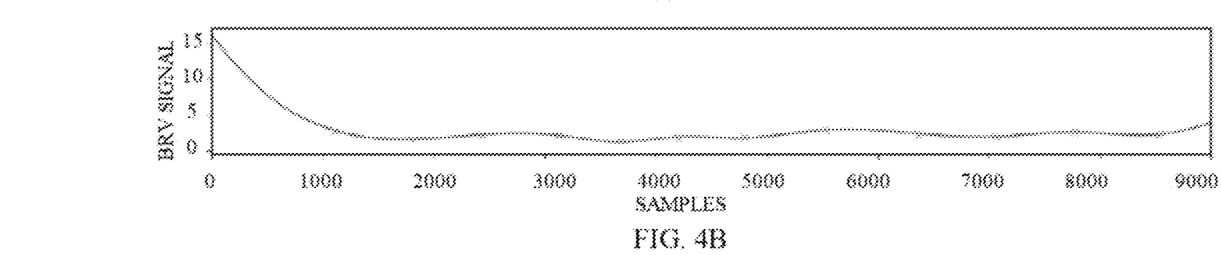

FIG. 4A shows the eye tracker data with the detected blink positions. Let the blinks occur at samples $k_n$, where $n \in \{0, 1, \ldots, N-1\}$ indexes the blinks. The BRV series sequence is defined as: $y[l_n] = (k_{n+1} - k_n)$, where $l_n = M(k_{n+1} + k_n)/2$ and $M=10$ is the oversampling factor. The oversampling is required because the sequence does not have a uniform sampling interval. This sequence, $\{y[l_n]\}$ is interpolated using a cubic model to obtain the BRV signal sampled at 300 Hz, $y[l]$, $l \in \{0, 1, \ldots, L-1\}$, where $L \approx MkN-1$. This interpolated curve $y[l]$ is shown in FIG. 4B and the cross marks correspond to $y[l_n]$.

Figure 4C:
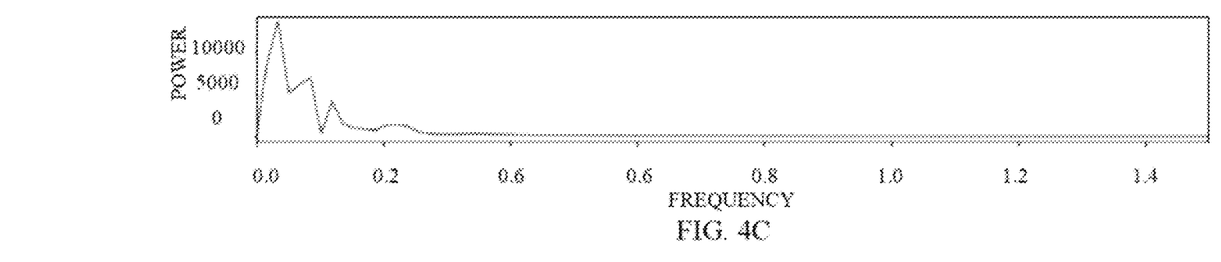

For analyzing the BRV series signal, six frequency and five time domain features were calculated. Time domain features included mean, median, standard deviation (STD), kurtosis and skewness of BRV series signal. For calculating the frequency domain features, fast-Fourier transform of the uniformly sampled BRV series signal was performed. FIG. 4C shows the spectrum of the BRV signal. Frequency domain features including mean frequency, power at mean frequency, dominant frequency, power at dominant frequency and total power, were calculated. In addition, a new feature called pareto frequency was introduced. Pareto principle states that, 80% of the effects come from 20% causes, hence, we calculated cumulative sum of powers up to 80% of the total power. This value is thus taken as the pareto frequency. Thus, it is the frequency below which 80% of signal power resides. Hence, in total 11 features were calculated for each BRV series signal.

Detail results of the analysis is presented below. Results of Stimulus 1 (reading and visual search task) Table 1 details the time and frequency domain features for stimulus 1 (baseline, reading task, visual search tasks 1 and 2).

TABLE 1

Average ± SD values of features for stimulus 1

| Features | Baseline | Reading | Task1 | Task2 |
|---|---|---|---|---|
| Pareto frequency | 0.16 ± 0.12 | 0.09 ± 0.06 | 0.06 ± 0.03 | 0.1 ± 0.06 |
| Mean Frequency | 0.24 ± 0.19 | 0.12 ± 0.09 | 0.13 ± 0.05 | 0.2 ± 0.11 |
| Power at mean frequency | 6e−21 ± 1e−20 | 4e−21 ± 9e−21 | 4e−23 ± 9e−22 | 4e−22 ± 8e−22 |
| Dominant frequency | 0.04 ± 0.05 | 0.04 ± 0.04 | 0.02 ± 0.01 | 0.03 ± 0.03 |
| Power at dominant frequency | 0.29 ± 0.22 | 0.33 ± 0.11 | 0.42 ± 0.11 | 0.33 ± 0.17 |
| Total power | 39.70e5 ± 11.47e6 | 42.07e4 ± 54.63e4 | 88.46e11 ± 27.81e12 | 35.63e7 ± 93.06e7 |
| Mean | 2.69 ± 1.04 | 3.88 ± 2.23 | 5.75 ± 3.44 | 6.24 ± 3.54 |
| Median | 1.78 ± 0.68 | 3.03 ± 1.94 | 4.59 ± 4.64 | 4.45 ± 4.34 |
| STD | 2.92 ± 1.83 | 3.36 ± 2.21 | 5.06 ± 2.63 | 5.6 ± 2.84 |
| Kurtosis | 3.62 ± 3.67 | 2.03 ± 3.17 | 0.43 ± 0.81 | 0.07 ± 0.93 |
| Skewness | 1.77 ± 0.92 | 1.35 ± 0.85 | 0.64 ± 0.66 | 0.78 ± 0.81 |

Figure 5:
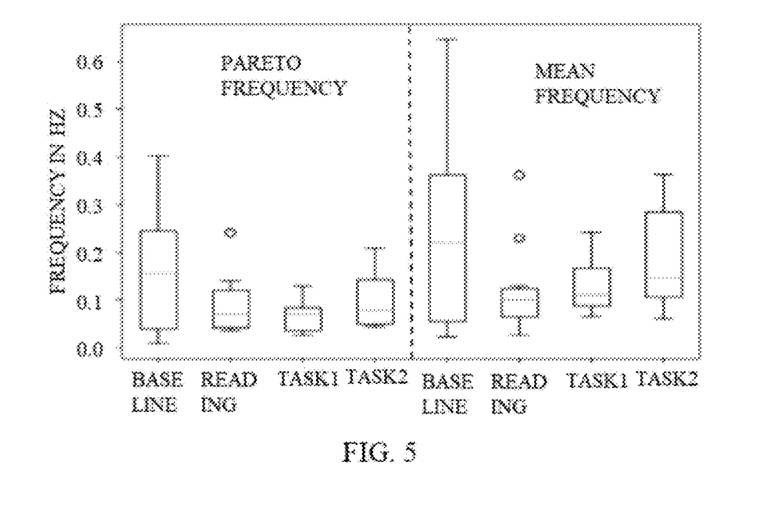
FIG. 5 illustrate Kurtosis and Skewness for stimulus 1 (of FIG. 3A), in accordance with some embodiments of the present disclosure.

The feature values have been averaged across subjects. From the table we observe that two time domain features namely, skewness and kurtosis shows variations across baseline and various tasks. Both kurtosis and skewness decrease as attention level increases from baseline to reading task and to visual search tasks. Skewness is the measure of symmetry of the probability density function of the amplitudes of the time series. On the other hand, kurtosis measures the amount of probability in tails. Acceptable range of skewness is (−1,1) and kurtosis is (−3,3) for normal distribution. From the values shown in Table 1 we observe that as attention increases (from baseline to reading, task 1 and task 2), skewness and kurtosis values obtained indicates that the curves tends towards a normal distribution. It was also observed that as attention increase, the inter blink interval becomes uniform leading to the conclusion that as attention increase, BRV becomes uniform. Thus, as attention increases, BRV becomes more and more uniform. FIG. 5 shows the boxplot of kurtosis and skewness for various tasks of stimulus 1. As is seen the mean value of kurtosis and skewness at baseline is maximum and decreases with increase in attention for reading and search tasks.

Figure 6:
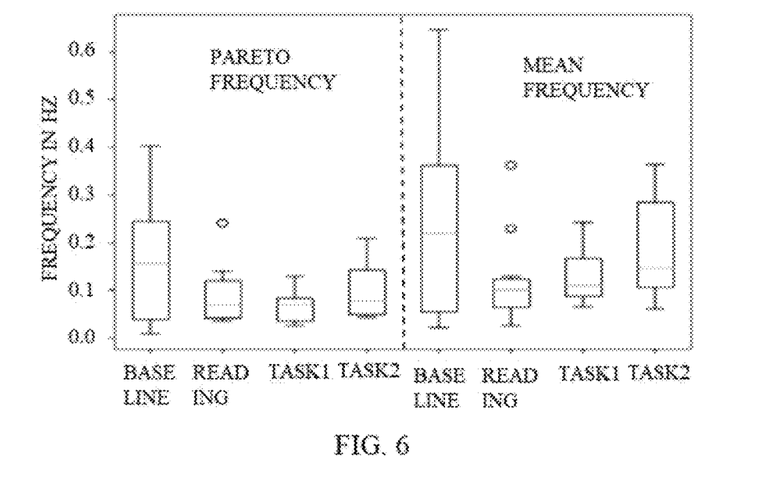
FIG. 6 illustrate Pareto and Mean frequency for stimulus 1 (of FIG. 3A), in accordance with some embodiments of the present disclosure.
Figure 7A:
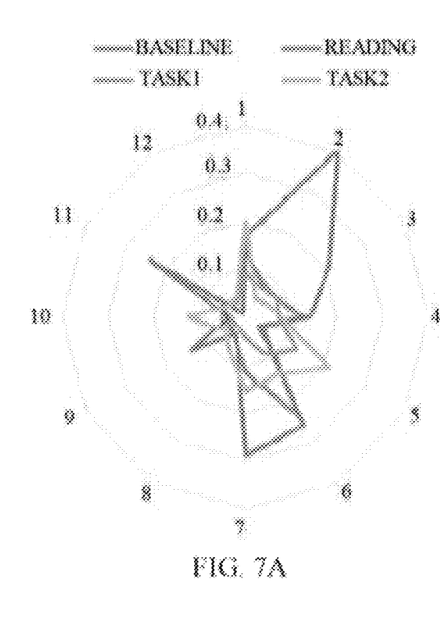
FIGS. 7A-7B illustrate spider plots of the pareto frequency for stimulus 1 and stimulus 2, respectively in accordance with some embodiments of the present disclosure.

Also, two frequency domain features namely, pareto frequency and mean frequency show notable variations as the attention increases. Both these feature values decrease as the attention level increases. FIG. 6 shows the boxplot of pareto frequency and mean frequency for stimulus 1. Both pareto and mean frequencies have maximum mean value at baseline and decreases with increase in attention level. FIG. 7A shows the spread of pareto frequency for the same. It was observed that as the attentional demand increases, the pareto frequency values are below 0.2 Hz. On the other hand, the pareto frequency increases up to 0.4 Hz for the baseline wherein not much visual attention is required. Thus, with increase in attention, the variability of the inter blink values reduces resulting in a more compact frequency bin and it spans across higher frequencies with decrease in attention. Similar plot was obtained for mean frequency as well and is skipped for the sake of brevity.

Table 2 depicts various time and frequency domain features for stimulus 2 (DSST task).

TABLE 2

Average ± SD values of features for stimulus 2

| Features | Version 1 | Version2 | Version3 |
|---|---|---|---|
| Pareto frequency | 0.08 ± 0.07 | 0.1 ± 0.07 | 0.11 ± 0.08 |
| Mean Frequency | 0.16 ± 0.11 | 0.18 ± 0.12 | 0.18 ± 0.13 |
| Power at mean frequency | 8e−23 ± 1e−23 | 4e−22 ± 1e−22 | 1e−23 ± 2e−23 |
| Dominant frequency | 0.02 ± 0.01 | 0.03 ± 0.04 | 0.02 ± 0.02 |
| Power at dominant frequency | 0.32 ± 0.16 | 0.25 ± 0.17 | 0.23 ± 0.13 |
| Total power | 34.49e10 ± 15.66e11 | 48.46e7 ± 18.26e8 | 17.64e7 ± 35.83e7 |
| Mean | 7.45 ± 4.25 | 5.72 ± 4.41 | 7.19 ± 5.66 |
| Median | 5.68 ± 4.18 | 4.75 ± 4.56 | 5.88 ± 5.17 |
| STD | 6.38 ± 4.17 | 4.29 ± 3.28 | 5.92 ± 5.06 |
| Kurtosis | 1.67 ± 3.31 | 1.81 ± 4.43 | 1.49 ± 2.34 |
| Skewness | 1.25 ± 0.9 | 1.08 ± 1.0 | 1.24 ± 0.78 |

Figure 7B:
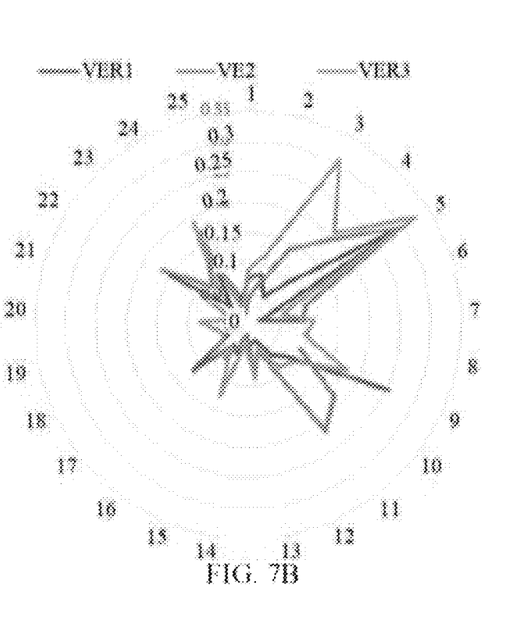

The feature values have been averaged across subjects. For the DSST task, since all the 3 versions require attention, the uniformity in the feature values is noticed. For all the three versions, kurtosis and skewness values are almost comparable. The pareto frequency values for stimulus 2 are shown in FIG. 7B. Since, all the 3 versions of DSST require visual attention, there is no difference in the pareto frequencies across versions and the values are compact below 0.3 Hz. It is to be noted that the frequency span in this case is also very compact as seen for reading and visual search tasks which also require increased attention levels. For stimulus 1, the average mean frequency and average pareto frequency are 0.24 Hz and 0.16 Hz, respectively, during the baseline period. As the attention increases, the average mean frequency and pareto frequency obtained are 0.14 Hz and 0.08 Hz respectively. Similar results are obtained for DSST task also. In version 1, 2 and 3 of DSST task, the attention values are high resulting in average mean frequency values: 0.15, 0.17 and 0.18 Hz (for 3 versions, respectively) and pareto frequencies: 0.08, 0.1 and 0.105 Hz (for 3 versions, respectively).

Thus, as attention increases, variability in inter-blink intervals reduces, resulting in reduced frequency span and the BRV probability distribution function of amplitudes follows normal distribution. Hence, kurtosis, skewness, pareto frequency and mean frequency are reliable markers of sustained attention. For stimulus 2 (all 3 versions), which require attention, the pareto frequency values were always <0.1 Hz. In case of stimulus 1, four participants did not show any variations in blink rate across tasks. For remaining participants pareto frequency was <0.1 Hz for tasks requiring attention. Thus, we can consider a Pareto frequency <0.1 Hz as a good marker for high attention level.

The pareto frequency values for stimulus 2 are shown in FIG. 7B. Since, all the 3 versions of DSST require visual attention, no difference was found in the pareto frequencies across versions and the values are compact below 0.3 Hz. It is to be noted that the frequency span in this case is also very compact as seen for reading and visual search tasks which also require increased attention levels. For stimulus 1, the average mean frequency and average pareto frequency are 0.24 Hz and 0.16 Hz, respectively, during the baseline period. As the attention increases, the average mean frequency and pareto frequency obtained are 0.14 Hz and 0.08 Hz respectively. Similar results are obtained for DSST task also. In version 1, 2 and 3 of DSST task, the attention values are high resulting in average mean frequency values: 0.15, 0.17 and 0.18 Hz (for 3 versions, respectively) and pareto frequencies: 0.08, 0.1 and 0.105 Hz (for 3 versions, respectively). Thus, we can conclude that as attention increases, variability in inter-blink intervals reduces, resulting in reduced frequency span and the BRV probability distribution function of amplitudes follows normal distribution. Hence, kurtosis, skewness, pareto frequency and mean frequency are reliable markers of sustained attention. For stimulus 2 (all 3 versions), which require attention, the pareto frequency values were always <0.1 Hz. In case of stimulus 1, four participants did not show any variations in blink rate across tasks. For remaining participants pareto frequency was <0.1 Hz for tasks requiring attention. Thus, the Pareto frequency <0.1 Hz is a good marker for high attention level.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Recently, researches are being conducted for relating the blink rate variability (BRV) with various cognitive performances. A BRV is a time series constructed from intervals between consecutive eye-blinks. A variety of time domain and frequency domain features of the BRV signal have been used for assessment of cognitive performances. However, to the best of our knowledge, a detail analysis of frequency domain features of BRV and the application of the same for measurement of sustained attention has not been studied so far. In this study, we have recorded eye blinks using an eye tracker while the participants were resting and performing visual tasks. Detailed analysis of blink response reveals that BRV is a potential marker of sustained attention.

Various embodiments disclosed herein provides method and system for eye-blink based assessment of visual sustained attention of a target. For example, in one embodiment, the disclosed system records gaze data of user, for example, a human being, and obtains BRV series signal therefrom. The system extracts frequency domain features including the pareto frequency feature from the uniformly sampled BRV series signal. The sustained attention of the target is determined based at least on a comparison of the value of the pareto frequency feature with a threshold value of the pareto frequency for sustained attention indicative of the visual attention is less than or equal to 0.1 Hz. Thus, this value of pareto frequency is used as the ground truth for deciding the attention level of the targets. Based on various embodiments, BRV can be used as a marker of sustained attention in a visual task.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for assessing sustained visual attention of a target comprising:
    recording gaze data of the target using an eye tracker, via one or more hardware processors, the gaze data comprising data associated with eye-blink response of the target during a systematic execution of a set of visual tasks;
    reconstructing from the gaze data, a set of uniformly sampled blink rate variability (BRV) series signals via the one or more hardware processors, each of the BRV series signals comprises a time series data constructed from intervals between consecutive eye-blinks obtained during the systematic execution of the set of visual tasks, wherein reconstructing a uniformly sampled BRV series signal from amongst the set of uniformly sampled BRV series signals comprises performing oversampling and interpolation on the gaze data;
    extracting, via the one or more hardware processors, one or more time and frequency domain features from the set of uniformly sampled BRV series signals, wherein the one or more frequency domain features comprises at least a pareto frequency feature;
    comparing values of the one or more features of the set of BRV series signals with a threshold values of the one or more features that are indicative of visual attention via the one or more hardware processors; and
    determining, via the one or more hardware processors, visual sustained attention of the target based on the comparison.

2. The method of claim 1, wherein the pareto frequency feature comprises a frequency range within which 80% of cumulative power of a frequency spectrum of the BRV series signals resides.

3. The method of claim 1, wherein the gaze data is obtained by systematically recording eye movements and eyelid movements during the set of visual tasks.

4. The method of claim 1, wherein the eye tracker is one of an Infrared based eye tracker and a camera based eye tracker.

5. The method of claim 1, wherein the one or more frequency domain features further comprises frequency, power at mean frequency, dominant frequency, power at dominant frequency and total power.

6. The method of claim 1, further comprises identifying the eye blink positions in the gaze data, and wherein a point in the gaze data is treated as eye blink on performance of one of: determination of occurrence of a threshold number of consecutive zeros and missing data point in the gaze data.

7. The method of claim 1, wherein calculating the one or more frequency domain features comprises performing fast-Fourier transform of the uniformly sampled BRV series.

8. The method of claim 1, wherein the threshold value of the pareto frequency feature indicative of the visual attention is less than or equal to 0.1 Hz.

9. A system for assessing visual sustained attention of a target, comprising:
    a memory storing instructions;
    one or more communication interfaces; and
    one or more hardware processors coupled to the memory via the one or more communication interfaces, wherein the one or more hardware processors are configured by the instructions to:
    record gaze data of the target using an eye tracker the gaze data comprising data associated with eye-blink response of the target during a systematic execution of a set of visual tasks;
    reconstruct from the gaze data, a set of uniformly sampled blink rate variability (BRV) series signals, each of the BRV series comprises a time series data constructed from intervals between consecutive eye-blinks obtained during the systematic execution of a set of visual tasks, wherein to reconstruct a uniformly sampled BRV series signal from amongst the set of uniformly sampled BRV series signals, the one or more hardware processors are further configured by the instructions to perform oversampling and interpolation on the gaze data;
    extract one or more time and frequency domain features from the set of uniformly sampled BRV series signals, wherein the one or more frequency domain features comprises at least a pareto frequency feature;
    compare values of the one or more features of the set of BRV series signals with a threshold values of the one or more features that are indicative of visual attention; and
    determine visual sustained attention of the target based on the comparison.

10. The system of claim 9, wherein the pareto frequency feature comprises a frequency range within which 80% of cumulative power of a frequency spectrum of the BRV series signal resides.

11. The system of claim 9, wherein the one or more hardware processors are further configured by the instructions to obtain the gaze data by systematically recording eye movements and eyelid movements during the set of visual tasks.

12. The system of claim 9, wherein the eye tracker is one of an Infrared based eye tracker and a camera based eye tracker.

13. The system of claim 9, wherein the one or more frequency domain features further comprises frequency, power at mean frequency, dominant frequency, power at dominant frequency and total power.

14. The system of claim 9, wherein the one or more hardware processors are further configured by the instructions to identify the eye blink positions in the gaze data, further wherein the one or more hardware processors are configured by the instructions to treat a point in the gaze data as eye blink on performance of one of: determination of occurrence of a threshold number of consecutive zeros and missing data point in the gaze data.

15. The system of claim 9, wherein the one or more hardware processors calculating the one or more frequency domain features comprises performing fast-Fourier transform of the uniformly sampled BRV series.

16. The system of claim 9, wherein the threshold value of the pareto frequency feature indicative of the visual attention is less than or equal to 0.1 Hz.

17. One or more non-transitory machine readable information storage mediums comprising one or more instructions which when executed by one or more hardware processors cause:
  recording gaze data of the target using an eye tracker, via one or more hardware processors, the gaze data comprising data associated with eye-blink response of the target during a systematic execution of a set of visual tasks;
  reconstructing from the gaze data, a set of uniformly sampled blink rate variability (BRV) series signals via the one or more hardware processors, each of the BRV series signals comprises a time series data constructed from intervals between consecutive eye-blinks obtained during the systematic execution of the set of visual tasks, wherein reconstructing a uniformly sampled BRV series signal from amongst the set of uniformly sampled BRV series signals comprises performing oversampling and interpolation on the gaze data;
  extracting, via the one or more hardware processors, one or more time and frequency domain features from the set of uniformly sampled BRV series signals, wherein the one or more frequency domain features comprises at least a pareto frequency feature;
  comparing values of the one or more features of the set of BRV series signals with a threshold values of the one or more features that are indicative of visual attention via the one or more hardware processors; and
  determining, via the one or more hardware processors, visual sustained attention of the target based on the comparison.

* * * * *